US006987158B2

(12) United States Patent
Laas et al.

(10) Patent No.: US 6,987,158 B2
(45) Date of Patent: *Jan. 17, 2006

(54) POLYADDUCTS CONTAINING URETIDONE GROUPS

(75) Inventors: Hans-Josef Laas, Bergisch Gladbach (DE); Reinhard Halpaap, Odenthal (DE); Peter Thometzek, Bergisch Gladbach (DE); Michael Grahl, Leverkusen (DE); Hans-Ulrich Meier-Westhues, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 129 days.

This patent is subject to a terminal disclaimer.

(21) Appl. No.: 10/613,725

(22) Filed: Jul. 3, 2003

(65) Prior Publication Data

US 2004/0059082 A1 Mar. 25, 2004

(30) Foreign Application Priority Data

| Jul. 4, 2002 | (DE) | ................................ 102 30 063 |
| Sep. 17, 2002 | (DE) | ................................ 102 43 029 |
| Sep. 17, 2002 | (DE) | ................................ 102 43 030 |

(51) Int. Cl.
| C08G 18/79 | (2006.01) |
| C08G 18/80 | (2006.01) |
| C08G 18/73 | (2006.01) |
| C08G 18/75 | (2006.01) |
| C07D 229/00 | (2006.01) |

(52) U.S. Cl. ................ 528/45; 252/182.2; 252/182.21; 252/182.22; 525/440; 528/67; 528/73; 540/202; 544/222; 548/950; 548/951; 548/952

(58) Field of Classification Search ............. 252/182.2, 252/182.21, 182.22; 528/45, 67, 73; 525/440; 540/202; 544/222; 548/950, 951, 952
See application file for complete search history.

(56) References Cited

U.S. PATENT DOCUMENTS

| 3,223,584 | A | * | 12/1965 | Luckenbaugh et al. | 514/210.02 |
| 4,476,054 | A | | 10/1984 | Disteldorf et al. | 540/202 |
| 4,912,210 | A | | 3/1990 | Disteldorf et al. | 540/202 |
| 5,329,003 | A | | 7/1994 | Bruchmann | 540/202 |
| 5,548,057 | A | * | 8/1996 | Hirayama et al. | 528/67 |
| 5,596,066 | A | | 1/1997 | Laas et al. | 528/73 |
| 5,606,001 | A | * | 2/1997 | Shaffer | 528/49 |
| 5,621,064 | A | | 4/1997 | Laas et al. | 528/60 |
| 5,814,689 | A | | 9/1998 | Goldstein et al. | 524/86 |
| 5,852,101 | A | | 12/1998 | Halpaap et al. | 524/507 |
| 5,861,193 | A | | 1/1999 | Goldstein et al. | 427/385.5 |
| 5,916,629 | A | | 6/1999 | Wenning et al. | 427/207.1 |
| 6,043,332 | A | | 3/2000 | Laas et al. | 528/51 |
| 6,297,343 | B1 | | 10/2001 | Laas et al. | 528/45 |
| 6,423,777 | B1 | | 7/2002 | Laas et al. | 525/127 |
| 6,479,613 | B2 | | 11/2002 | Gras et al. | 528/73 |
| 6,624,301 | B1 | | 9/2003 | Schmitt et al. | 540/202 |
| 2002/0062000 | A1 | | 5/2002 | Gras et al. | 528/73 |

FOREIGN PATENT DOCUMENTS

| CA | 2210272 | 1/1998 |
| DE | 197 28 855 | 1/1999 |
| EP | 0 735 027 | 9/1997 |

* cited by examiner

Primary Examiner—Rabon Sergent
(74) Attorney, Agent, or Firm—Joseph C. Gil

(57) ABSTRACT

Polyaddition compounds containing uretdione groups prepared by reacting uretdione polyisocyanates formed from diisocyanates having exclusively secondary- and/or tertiary-attached isocyanate groups with a molar fraction of isocyanurate structures, based on the sum of uretdione groups and isocyanurate groups, of not more than 10%, with compounds reactive towards isocyanates. The polyaddition compounds can be use as a starting component in the preparation of polyurethane plastics, in particular as crosslinkers for heat-crosslinkable powder coating materials. The compounds may be used as starting components in the preparation of moldings and shaped parts, and as starting components in the preparation of coating materials and coatings.

8 Claims, No Drawings

POLYADDUCTS CONTAINING URETIDONE GROUPS

The invention relates to novel polyaddition compounds containing uretdione groups, to a process for preparing them and to their use as a starting component in the preparation of polyurethane plastics, in particular as crosslinkers for heat-crosslinkable powder coating materials.

As blocking-agent-free crosslinkers for highly weather-stable polyurethane (PU) powder coating materials use is today made increasingly of polyaddition compounds containing uretdione groups. The crosslinking principle utilized in these compounds is the thermal cleavage of the uretdione structures back into free isocyanate groups and the subsequent reaction thereof with a hydroxy-functional binder.

The uretdione powder coating crosslinkers available on the market today are based without exception on linear dimers, i.e. dimers free from isocyanate groups, of 1-isocyanato-3,3,5-trimethyl-5-isocyanatomethylcyclohexane (isophorone diisocyanate; IPDI). Although experience with blocked PU powder coating crosslinkers shows that products based on 4,4'-diisocyanatodicyclohexylmethane possess advantageous properties as compared with the corresponding IPDI crosslinkers, possessing for example a greater reactivity and leading to coatings of much higher elasticity (cf. e.g. EP-A 0 517 028), uretdione powder coating crosslinkers of 4,4'-diisocyanatodicyclohexylmethane are to date unknown. Although a range of publications, e.g. EP-A 0 639 598, EP-A 0 669 354, EP-A 0 720 994, EP-A 0 818 482, EP-A 0 818 483, EP-A 0 818 484, DE-A 197 28 855, WO 99/11690, EP-A 1 024 158, EP-A 1 063 251 or EP-A 1 083 209, within long lists of diisocyanates suitable for preparing uretdione crosslinkers, includes 4,4'-diisocyanatodicyclohexylmethane in passing as a possible starting diisocyanate, in none of these disclosures is there any concrete description of a corresponding product. The reason for this is that with the state of the art dimerization catalysts it was hitherto impossible to prepare from 4,4'-diisocyanatodicyclohexylmethane a uretdione polyisocyanate at least substantially free from isocyanurate groups, as required as a starting compound for uretdione powder coating crosslinkers.

Whereas a variety of processes exist (e.g. EP-A 0 045 995, EP-A 0 317 744, EP-A 0 735 027 and EP-A 0 896 973) for the linear catalytic dimerization of aliphatic and/or cycloaliphatic diisocyanates having at least one primary-attached isocyanate group, such as 1,6-diisocyanatohexane (HDI) or 1-isocyanato-3,3,5-trimethyl-5-isocyanatomethylcyclohexane (isophoronediisocyanate; IPDI), for example, there has to date been no disclosure of uretdione polyisocyanates which are free from isocyanurate groups and derive from aliphatic and/or cycloaliphatic diisocyanates with exclusively secondary- and/or tertiary-attached isocyanate groups, such as 4,4'-diisocyanatodicyclohexylmethane, for example. The activity of the customary dimerization catalysts in respect of such diisocyanates is absent or, if present, is so low that when they are used, even in very high concentrations, the corresponding dimers can be prepared only in a vanishingly small yield, if at all.

The preparation of the polyadducts of the invention containing uretdione groups became possible only when a highly reactive and selective catalyst for the dimerization of diisocyanates having exclusively secondary- and/or tertiary-attached isocyanate groups was found that makes it possible to prepare substantially linear uretdione polyisocyanates which are preferably free from isocyanurate groups.

The preparation of uretdione polyisocyanates from aliphatic and/or cycloaliphatic diisocyanates having exclusively secondary- and/or tertiary-attached isocyanate groups is described below. It takes place by catalytic dimerization in the presence of special saltlike oligomerization catalysts containing 1,2,3- and/or 1,2,4-triazolate structures in the anion.

The present invention provides polyaddition compounds containing uretdione groups, obtainable by reacting uretdione polyisocyanates formed from diisocyanates having exclusively secondary- and/or tertiary-attached isocyanate groups with a molar fraction of isocyanurate structures, based on the sum of uretdione groups and isocyanurate groups, of not more than 10%, with compounds reactive towards isocyanates.

The invention also provides a process for preparing these polyaddition compounds, in which
A) uretdione polyisocyanates formed by diisocyanates having exclusively secondary- and/or tertiary-attached isocyanate groups, with a molar fraction of isocyanurate structures, based on the sum of uretdione groups and isocyanurate groups, of not more than 10%, together where appropriate with the use of
B) further diisocyanates and/or polyisocyanates in an amount of up to 70% by weight, based on the total weight of components A) and B), are reacted with
C) polyols of the molecular weight range from 62 to 2 000 and optionally
D) further isocyanate-reactive monofunctional compounds in an amount of up to 40% by weight, based on the total weight of components C) and D), while observing an equivalents ratio of isocyanate groups to isocyanate-reactive groups of from 1.8:1 to 0.6:1.

The invention also provides, finally, for the use of these polyaddition compounds containing uretdione groups as starting components in the preparation of polyurethane plastics, especially as crosslinker components in heat-crosslinkable two-component polyurethane powder coating materials for the coating of any heat-resistant substrates in accordance with the methods of powder coating technology.

Starting compounds A) for the process of the invention are uretdione polyisocyanates such as may be obtained by catalytic dimerization of some of the isocyanate groups of simple diisocyanates having exclusively secondary- and/or tertiary-attached isocyanate groups and, preferably, subsequent removal of the unreacted diisocyanate excess, for example by thin-film distillation. Suitable for preparing the starting compounds A) are aliphatic and/or cycloaliphatic diisocyanates having exclusively secondary- and/or tertiary-attached isocyanate groups, which may be prepared by any desired processes, for example by phosgenation or by a phosgene-free route, for example by urethane cleavage. The designation aliphatic or cycloaliphatic refers merely to the nature of the carbon atoms which carry the isocyanate groups; in other words, aromatic structures may indeed also be present in the molecule. Examples of suitable starting diisocyanates are 1,3- and/or 1,4-diisocyanatocyclohexane, 1,4-diisocyanato-3,3,5-trimethylcyclohexane, 1,3-diisocyanato-2-methylcyclohexane 1,3-diisocyanato-4-methylcyclohexane, 1,8-diisocyanato-p-menthane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 4,4'-diisocyanatodicyclohexylmethane, 4,4'-diisocyanato-3,3'-dimethyldicyclohexylmethane, 4,4'-diisocyanato-3,3',5,5'tetramethyldicyclohexylmethane, 1,3-diisocyanatoadamantane, 1,3-dimethyl-5,7- diisocyanatoadamantane, 1,3- and 1,4-bis(1-isocyanato-1-methylethyl)benzene (TMXDI) or bis(4-(1-isocyanato-1-methylethyl)phenyl) carbonate and also mixtures of such diisocyanates. Further diisocyanates, likewise suitable, having exclusively secondary- and/or tertiary-attached isocyanate groups can be found, furthermore, in, for example, Justus Liebigs Annalen der Chemie Volume 562, (1949) pp. 75–136.

Preferred diisocyanates for preparing the starting compounds A) are 4,4'-diisocyanatodicyclohexylmethane, 4,4'-diisocyanato-3,3'-dimethyldicyclohexylmethane, 1,3- and 1,4-diisocyanatocyclohexane and/or TMXDI. An especially preferred diisocyanate is 4,4'-diisocyanatodicyclohexylmethane.

The starting compounds A) are prepared from the aforementioned diisocyanates for example, by catalytic dimerization in the presence of special saltlike oligomerization catalysts containing 1,2,3- and/or 1,2,4-triazolate structures in the anion.

In this way by dimerization of aliphatic and/or cycloaliphatic isocyanates containing exclusively secondary and/or tertiary isocyanate groups it is possible to obtain compounds containing uretdione groups and having a molar fraction of isocyanurate structures, based on the sum of uretdione groups and isocyanurate groups, of not more than 10%.

Oligomerization catalysts employed in the process are any saltlike compounds containing 1,2,3- and/or 1,2,4-triazolate structures in the anion. These are compounds containing in the anion triazolate structures of the general formulae (I) and/or (II)

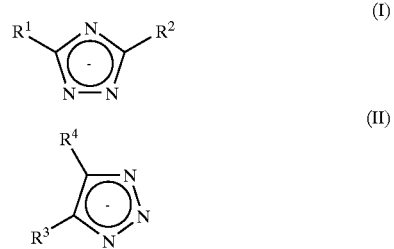

in which
$R^1$, $R^2$, $R^3$ and $R^4$ are identical or different radicals and are each a hydrogen atom, a halogen atom from the fluorine, chlorine or bromine series or a nitro group, a saturated or unsaturated aliphatic or cycloaliphatic radical or an optionally substituted aromatic or araliphatic radical which can contain up to 20 carbon atoms and optionally up to 3 heteroatoms from the oxygen, sulphur and nitrogen series and can be optionally substituted by halogen atoms or nitro groups, and where
$R^3$ and $R^4$ in formula (II) together with the carbon atoms of the 1,2,3-triazolate five-membered ring can also form fused rings having 3 to 6 carbon atoms.

Preferred oligomerization catalysts are those containing in the anion triazolate structures of the general formula (I) in which
$R^1$ and $R^2$ are identical or different radicals and are each a hydrogen atom, a halogen atom from the fluorine, chlorine or bromine series or a nitro group, a saturated aliphatic or cycloaliphatic radical or an optionally substituted aromatic or araliphatic radical which can contain up to 12 carbon atoms and optionally up to 3 heteroatoms from the oxygen, sulphur and nitrogen series and can optionally be substituted by halogen atoms or nitro groups.

Likewise preferred oligomerization catalysts are those containing in the anion triazolate structures of the general formula (II) in which
$R^3$ and $R^4$ are identical or different radicals and are each a hydrogen atom, a halogen atom from the fluorine, chlorine or bromine series or a nitro group, a saturated or unsaturated aliphatic or cycloaliphatic radical or an optionally substituted aromatic or araliphatic radical which can contain up to 12 carbon atoms and optionally up to 3 heteroatoms from the oxygen, sulphur and nitrogen series and can optionally be substituted by halogen atoms or nitro groups and together with the carbon atoms of the 1,2,3-triazolate five-membered ring can also form fused rings having 3 to 6 carbon atoms.

Particularly preferred oligomerization catalysts for the process are salts of 1,2,4-triazole, of 1,2,3-triazole and/or of 1,2,3-benzotriazole.

As counterions to the catalytically active triazolate anions the catalysts for use in accordance with the invention can contain any desired cations. Mention may be made here by way of example of alkali metal cations such as $Li^+$, $Na^+$ and $K^+$, alkaline earth metal cations such as $Mg^{2+}$ and $Ca^{2+}$, and ammonium or phosphonium cations, of the general formula (III),

in which
E is nitrogen or phosphorus,
$R^5$, $R^6$, $R^7$ and $R^8$ are identical or different radicals and are each a hydrogen atom, a saturated or unsaturated aliphatic or cycloaliphatic radical or an optionally substituted aromatic or araliphatic radical which can contain up to 24 carbon atoms and optionally up to 3 heteroatoms from the oxygen, sulphur and nitrogen series and can optionally be substituted by halogen atoms or hydroxyl groups, and where
$R^8$ can also be a radical of the formula (IV)

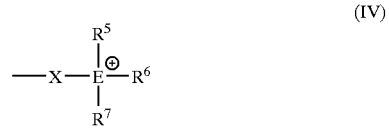

in which
X is a divalent, optionally substituted, aliphatic, cycloaliphatic, araliphatic or aromatic radical having up to 12 carbon atoms and
$R^5$, $R^6 R^7$ and E are as defined above.

Preferred cations are alkali metal ions or monovalent ammonium or phosphonium cations of the general formula (III) in which
E is nitrogen or phosphorus and
$R^5$, $R^6$, R and $R^8$ are identical or different radicals and are each a saturated aliphatic or cycloaliphatic radical or an optionally substituted aromatic or araliphatic radical having up to 18 carbon atoms.

The saltlike compounds used as oligomerization catalysts in the process are in some cases available commercially, in the form of their sodium salts, for example, and otherwise are readily obtainable by customary laboratory methods.

In the process these catalysts are employed generally in amounts of from 0.01 to 3% by weight, preferably from 0.1 to 2% by weight, based on the amount of isocyanate employed. They can be added to the reaction mixture in bulk; optionally, however, the catalysts may also be used in solution in a suitable organic solvent. The degree of dilution of the catalyst solutions may in this case be chosen freely within a very broad range. Catalytically active solutions are those with a concentration of or above 0.01% by weight Examples of suitable catalyst solvents are solvents which are inert towards isocyanate groups, such as hexane, toluene, xylene, chlorobenzene, ethyl acetate, butyl acetate, diethylene glycol dimethyl ether, dipropylene glycol dimethyl ether, ethylene glycol monomethyl or monoethyl ether acetate, diethylene glycol ethyl and butyl ether acetate, propylene glycol monomethyl ether acetate, 1-methoxyprop-2-yl acetate, 3-methoxy-n-butyl acetate, propylene glycol diacetate, acetone, methyl ethyl ketone, methyl isobutyl ketone, cyclohexanone, lactones such as β-propiolactone, γ-butyrolactone, ε-caprolactone and ε-methyl caprolactone, for example, but also solvents such as N-methylpyrrolidone and N-methylcaprolactam, 1,2-propylene carbonate, methylene chloride, dimethyl sulphoxide, triethyl phosphate or any mixtures of such solvents.

If catalyst solvents are employed at all in the process of the invention, they are preferably those which carry isocyanate-reactive groups and are incorporated in the reaction product. Examples of such solvents are monohydric or polyhydric simple alcohols, such as methanol, ethanol, n-propanol, isopropanol, n-butanol, n-hexanol, 2-ethyl-1-hexanol, ethylene glycol, propylene glycol, the isomeric butanediols, 2-ethyl-1,3-hexanediol or glycerol; ether alcohols, such as 1-methoxy-2-propanol, 3-ethyl-3-hydroxymethyloxetane, tetrahydrofurfuryl alcohol, ethylene glycol monomethyl ether, ethylene glycol monoethyl ether, ethylene glycol monobutyl ether diethylene glycol monomethyl ether, diethylene glycol monoethyl ether, diethylene glycol monobutyl ether, diethylene glycol, dipropylene glycol or else liquid higher-molecular-mass polyethylene glycols, polypropylene glycols, mixed polyethylene/polypropylene glycols and also the monoalkyl ethers thereof; ester alcohols, such as ethylene glycol monoacetate, propylene glycol monolaurate, glyceryl monoacetate and diacetate, glyceryl monobutyrate or 2,2,4-trimethyl-1,3-pentanediol monoisobutyrate; unsaturated alcohols such as allyl alcohol, 1,1-dimethyl allyl alcohol or oleyl alcohol; araliphatic alcohols such as benzyl alcohol; N-monosubstituted amides, such as N-methylformamide, N-methylacetamide, cyanoacetamide or 2-pyrrolidinone, for example, or any mixtures of such solvents.

If desired, especially when reacting diisocyanates, the oligomerization reaction in the process of the invention is terminated at the desired degree of conversion—for example, when from 10 to 60% of the isocyanate groups originally present in the starting mixture have reacted—with the aid of suitable catalyst poisons. Examples of such catalyst poisons are inorganic acids such as hydrochloric acid, phosphorous acid or phosphoric acid, acid chlorides such as acetyl chloride, benzoyl chloride or isophthaloyl dichloride, sulphonic acids and sulphonic esters, such as methanesulphonic acid, p-toluenesulphonic acid, trifluoromethanesulphonic acid, perfluorobutanesulphonic acid, dodecylbenzenesulphonic acid, methyl p-toluenesulphonate and ethyl p-toluenesulphonate, monoalkyl and dialkyl phosphates such as monotridecyl phosphate, dibutyl phosphate and dioctyl phosphate, but also silylated acids, such as trimethylsilyl methanesulphonate, trimethylsilyl trifluoromethanesulphonate, tris(trimethylsilyl) phosphate and diethyl trimethylsilyl phosphate.

The amount of the catalyst poison needed to stop the reaction is guided by the molar amount of the catalyst used; generally speaking, an equivalent molar amount of the stopping agent, based on the oligomerization catalyst used to start with, is employed. However, taking into account possible catalyst losses during the reaction, it may be sufficient to stop the reaction using just 20 to 80 mol % of the catalyst poison, based on the molar amount of catalyst originally employed.

The aforementioned catalyst poisons may be used either in bulk or in solution in a suitable organic solvent. Suitable solvents are, for example, the solvents already described above as possible catalyst solvents, or mixtures thereof. The degree of dilution can be chosen freely within a very broad range: suitable solutions, for example, are those with a concentration of or above 10% by weight.

In addition to the organic solvents mentioned, the abovementioned starting isocyanates containing exclusively secondary and/or tertiary isocyanate groups may also act as solvents for the catalyst poisons in the process of the invention provided that they are sufficiently inert towards isocyanate groups, and so allow storage-stable solutions to be prepared.

In the process it is also possible if desired to use additives customary in polyurethane chemistry as stabilizers. Such additives are, for example, phenolic antioxidants, such as 2,6-di-tert-butyl-4-methylphenol, 2,4,6-tri-tert-butylphenol and 3,5-di-tert-butyl-4-hydroxyanisole, for example, or phosphite stabilizers trisubstituted by alkyl and/or aryl radicals, such as triphenyl phosphite, tris(nonylphenyl) phosphite, diphenyl isooctyl phosphite, diphenyl isodecyl phosphite, diisodecyl phenyl phosphite, diisooctyl octyl phenyl phosphite, phenyl neopentyl glycol phosphite, 2,4,6-tri-tert-butylphenyl 2-butyl-2-ethyl-1,3-propanediol phosphite, triisodecyl phosphite, trilauryl phosphite, tris(tridecyl) phosphite, diisodecyl pentaerythritol diphosphite, distearyl pentaerythritol diphosphite, bis(2,4-di-tert-butylphenyl) pentaerythritol diphosphite and tetraphenyl dipropylene glycol diphosphite or any mixtures of such additives.

If these additives are used at all, they are added to the reaction mixture in an amount of up to 5% by weight, preferably up to 3% by weight, based on the amount of starting isocyanates employed.

In one particular embodiment of the process for preparing the strating compounds A), additives of the type specified which are liquid at room temperature, preferably the liquid phosphite stabilizers mentioned, serve as solvents for the catalysts and/or catalyst poisons employed.

Apart from any catalyst solvents and/or stopper solvents which may be used, the process for preparing the starting compounds A) is conducted preferably in bulk. However it can also be carried out if desired in the presence of further amounts of solvents which are inert towards isocyanate groups. Suitable examples include the non-reactive solvents already described above as possible catalyst solvents, or any desired mixtures of these solvents, which can be used optionally in an amount of up to 80% by weight, based on the total amount of starting isocyanates and added solvent.

To carry out the process the stated starting compounds containing exclusively secondary and/or tertiary isocyanate groups are charged optionally under inert gas such as nitrogen, for example, optionally in the presence of a suitable solvent and optionally of a stabilizer of the type specified to a vessel at a temperature of from 0 to 100° C., preferably from 20 to 60° C. Then an oligomerization catalyst or a solution of an oligomerization catalyst of the abovementioned type is added in the amount indicated above and the reaction temperature is adjusted where appropriate by a suitable measure (heating or cooling) to a temperature of from 20 to 100° C., preferably from 25 to 80° C. The catalyst can be added in one or more portions or else continuously, using a suitable metering pump, for example, over the entire reaction time. The reaction can optionally be ended at a target degree of oligomerization—for example, on reaching a degree of oligomerization of from 10 to 60%, preferably from 10 to 40%—by addition of a catalyst poison of the type exemplified and optionally subsequent brief heating of the reaction mixture at, for example, a temperature lying above 80° C. By "degree of oligomerization" is meant here the percentage of the isocyanate groups originally present in the starting mixture (and corresponding to 100%) which is consumed during the reaction according to the invention (in particular by dimerization, additionally with trimerization and, in the case where the catalyst solvents described, for example alcoholic catalyst solvents, are used as well, by reaction with isocyanate groups involving urethanization, for example). The stated degree of oligomerization is generally reached after a reaction time of from 30 minutes to 8 hours, preferably from 1 to 6 hours.

The reaction mixture is preferably freed subsequently by thin-film distillation at pressures from 0.001 to 20 mbar, more preferably from 0.01 to 5 mbar, under conditions as gentle as possible, for example at a temperature of from 120 to 220° C., preferably from 140 to 190° C., from volatile constituents (excess monomeric starting isocyanates and any non-reactive solvents and stabilizers used).

In another embodiment of the process of the invention the stated volatile constituents are separated off from the oligomerization product by extraction with suitable solvents which are inert towards isocyanate groups, examples being aliphatic or cycloaliphatic hydrocarbons such as pentane, hexane, heptane, cyclopentane or cyclohexane.

The distillates obtained, which in addition to unreacted monomeric starting isocyanates contain any solvents and stabilizers used and also, in the absence of a catalyst poison, may contain active catalyst, can be readily used for further oligomerization.

With the process for preparing the starting compounds A) it is possible if desired, following partial catalytic polymerization and termination of the reaction at the target degree of oligomerization by addition of a catalyst poison, to dispense with the removal of the excess, unreacted starting diisocyanate. In this case the process products obtained are pale-coloured solutions of compounds containing uretdione groups in up to 70% by weight of monomeric starting isocyanate.

This process for preparing the starting compounds A) permits for the first time the dimerization of secondary and/or tertiary isocyanate groups in a simple way using very low catalyst concentrations and within very short reaction times.

The uretdione polyisocyanates obtainable by this process from diisocyanates containing exclusively secondary and/or tertiary isocyanate groups, or solutions of the said polyisocyanates in monomeric starting diisocyanates, constitute valuable starting materials A) for the preparation of uretdione powder coating crosslinkers. Furthermore, they are suitable for the preparation of polyurethane polymers by the polyaddition process, preferably for the preparation of one-component or two-component polyurethane coating materials. In this context they can also be used as crosslinker components for one-component baking varnishes, in a form in which they have been blocked with blocking agents known per se from polyurethane chemistry. Examples of suitable blocking agents are the following compounds known from polyurethane chemistry as blocking agents for isocyanate groups: oximes, such as acetone oxime, butanone oxime and cyclohexanone oxime, for example, lactams, such as ε-caprolactam, C—H-acidic compounds, such as diethyl malonate and acetoacetates, N-heterocycles, such as 1,2,4-triazole, dimethyl-1,2,4-triazole, 3,5-dimethylpyrazole and imidazole, and any mixtures of these blockings agents.

Depending on the nature of the chosen starting diisocyanates and on the chosen degree of oligomerization, the starting compounds A) obtainable in this way have an isocyanate group content of from 11.2 to 25.4% by weight, preferably from 12.8 to 23.9% by weight, more preferably from 13.5 to 16.0% by weight and contain less than 5% by weight, preferably less than 2% by weight, more preferably less than 1% by weight of monomer diisocyanates. The molar fraction of isocyanurate structures in the starting compounds A), based on the sum of uretdione groups and isocyanurate groups; is not more than 10%, preferably not more than 8% and very preferably not more than 5%.

In the process of the invention, for preparing the polyaddition compounds, if desired, further diisocyanates and/or polyisocyanates B) may be used as well. These are, for example, any desired monomer diisocyanates having aliphatically, cycloaliphatically, araliphatically and/or aromatically attached isocyanate groups, particularly those of the molecular weight range 140 to 400, such as 1,4-diisocyanatobutane, 1,6-diisocyanatohexane (HDI), 1,5-diisocyanato-2,2-dimethylpentane, 2,2,4- and/or 2,4,4-trimethyl-1,6-diisocyanatohexane, 1,10-diisocyanatodecane, IPDI, 1-isocyanato-1-methyl-4(3)-isocyanatomethylcyclohexane, 1,3- and 1,4-phenylene diisocyanate, 2,4- and 2,6-tolylene diisocyanate, diphenylmethane 2,4'- and/or 4,4'-diisocyanate, naphthylene 1,5-diisocyanate, the diisocyanates described above in connection with the preparation of the starting compounds A) and having exclusively secondary-and/or tertiary-attached isocyanate groups, or any desired mixtures of such diisocyanates, and also polyisocyanates prepared by modification of these monomer diisocyanates and having uretdione, isocyanurate, urethane, allophanate, biuret and/or oxadiazinetrione structure, as described exemplarily in, for example, DE-A 1 670 666, DE-A 3 700 209 and DE-A 3 900 053 or in EP-A 0 336 205 and EP-A 0 339 396.

These diisocyanates and/or polyisocyanates B) are used, if at all, in amounts of up to 70% by weight, preferably up to 50% by weight, based on the total weight of components A) and B). Preferred starting components B) such as may optionally be used as well in the process of the invention are diisocyanates and polyisocyanates having aliphatically and/or cycloaliphatically attached isocyanate groups. Particularly preferred is the use of monomer HDI, IPDI and/or 4,4'-diisocyanatodicyclohexylmethane or polyisocyanates formed from HDI and/or IPDI having uretdione and/or isocyanurate structure.

Starting compounds C) for the process of the invention are polyols of the molecular weight range of 62–2 000 which have an (average) OH functionality of at least 2.0, or mixtures of such polyols.

Examples of suitable polyols C) are polyhydric alcohols of the molecular weight range 62 to 400, such as 1,2-ethanediol, 1,2- and 1,3-propanediol, the isomeric butanediols, pentanediols, hexanediols, heptanediols and octianediols, 1,2- and 1,4-cyclohexanediol, 1,4-cyclohexanedimethanol or 4,4'-(1-methyl-ethyl-idene)bis-cyclohexanol, 1,2,3-propanetriol, 1,1,1-trimethylolethane, 1,2,6-hexanetriol, 1,1,1-trimethylolpropane, 2,2-bis(hydroxymethyl)-1,3-propanediol or 1,3,5-tris(2-hydroxyethyl) isocyanurate, but also ester alcohols or ether alcohols, such as neopentylglycol hydroxypivalate, diethylene glycol or dipropylene glycol.

Suitable starting compounds C) are also the conventional polyhydroxyl compounds of the polyester, polycarbonate, polyester carbonate or polyether type.

Polyester polyols suitable as polyol components C) are, for example, those with a number-average molecular weight of from 200 to 2 000, preferably from 250 to 1 500, with a hydroxyl group content of from 1 to 21% by weight, preferably from 2 to 18% by weight, as may be prepared in conventional manner by reacting polyhydric alcohols, for example those mentioned above of the molecular weight range 62 to 400, with deficit amounts of polybasic carboxylic acids, corresponding carboxylic anhydrides, corresponding polycarboxylic esters of lower alcohols or lactones.

The acids or acid derivatives used to prepare the polyester polyols may be aliphatic, cycloaliphatic and/or aromatic in nature and may where appropriate be substituted, by halogen atoms for example, and/or unsaturated. Examples of suitable acids are polybasic carboxylic acids of the molecular weight range 118 to 300 or derivatives thereof, examples being succinic acid, adipinic acid, sebacic acid, phthalic acid, isophthalic acid, trimellitic acid, phthalic anhydride, tetrahydrophthalic acid, maleic acid, maleic anhydride, dimeric and trimeric fatty acids, dimethyl terephthalate and bisglycol terephthalate.

To prepare the polyester polyols it is also possible to use any desired mixtures of these exemplified starting compounds.

One kind of polyester polyols used with preference as polyol component C) are those preparable in conventional manner from lactones and simple polyhydric alcohols, such as those exemplified above, for example, as starter molecules with ring opening. Suitable lactones for preparing these polyester polyols are, for example, β-propiolactone, γ-butyrolactone, α- and β-valerolactone, ε-caprolactone, 3,5,5- and 3,3,5-trimethylcaprolactone or any desired mixtures of such lactones.

Polyhydroxyl compounds of the polycarbonate type that are suitable as polyols C) are in particular the polycarbonate diols, known per se, such as are preparable, for example, by reacting dihydric alcohols, for example those exemplified above in the list of the polyhydric alcohols of the molecular weight range 62 to 400, with dialkyl or diaryl carbonates, for example dimethyl or diphenyl carbonate, or phosgene.

Polyhydroxyl compounds of the polyester carbonate type that are suitable as polyols C) are in particular the conventional diols containing ester groups and carbonate groups, such as may be obtained, for example, in accordance with the teaching of DE-A 1 770 245 by reacting dihydric alcohols with lactones of the type exemplified above, especially ε-caprolactone, and then reacting the resulting polyester diols with diphenyl carbonate.

Polyether polyols suitable as polyols C) are in particular those with a number-average molecular weight of from 200 to 2 000, preferably 250 to 1 500, with a hydroxyl group content of from 1.7 to 25% by weight, preferably 2.2 to 20% by weight, such as are obtainable in conventional manner by alkoxylating suitable starter molecules. For preparing these polyether polyols it is possible to use as starter molecules any desired polyhydric alcohols, such as those described above of the molecular weight range 62 to 400. Alkylene oxides suitable for the alkoxylation reaction are, in particular, ethylene oxide and propylene oxide, which may be used in either order or else in a mixture for the alkoxylation reaction.

Further suitable polyether polyols include the conventional polyoxytetramethylene glycols such as may be obtained, for example, in accordance with Angew. Chem. 72, 927 (1960) by polymerization of tetrahydrofuran.

Likewise suitable as starting compounds C) are dimer diols, such as may be prepared in conventional manner, for example, by hydrogenating dimeric fatty acids and/or esters thereof in accordance with the process described in DE-A 1 768 313 or other processes described in EP-A 0 720 994 page 4, line 33 to line 58.

Preferred starting compounds C) for the process of the invention are the above-mentioned simple polyhydric alcohols of the molecular weight range 62 to 400, the stated polyester polyols or polycarbonate polyols, and also any desired mixtures of these polyol components.

Used with particular preference, however, are the diols of the molecular weight range 62 to 300, mentioned above within the list of the simple polyhydric alcohols; polyester diols or polycarbonate diols of the molecular weight range 134 to 1 200; or mixtures thereof.

Especially preferred starting compounds C) for the process of the invention are mixtures of the aforementioned polyester diols with up to 80% by weight, preferably up to 60% by weight, based on the total weight of the polyols C) used, of simple diols of the molecular weight range 62 to 300.

In the process of the invention it is also possible if desired to use still further isocyanate-reactive monofunctional compounds D) as well. These are, in particular, aliphatic or cycloaliphatic monoamines, such as methylamine, ethylamine, n-propylamine, isopropylamine, the isomeric butylamines, pentylamines, hexylamines and octylamines, n-dodecylamine, n-tetradecylamine, n-hexadecylamine, n-octadecylamine, cyclohexylamine, the isomeric methylcyclohexylamines and also aminomethylcyclohexane, secondary monoamines, such as dimethylamine, diethylamine, dipropylamine, diisopropylamine, dibutylamine, diisobutylamine, bis(2-ethylhexyl)amine, N-methyl- and N-ethylcyclohexylamine and also dicyclohexylamine or monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols and also hydroxymethylcyclohexane.

These monofunctional compounds D) are employed, if at all, in amounts of up to 40% by weight, preferably 25% by weight, based on the total amount of isocyanate-reactive starting compounds C) and D).

Preferred starting compounds D) for the process of the invention are the simple aliphatic or cycloaliphatic monoalcohols of the type mentioned.

To implement the process of the invention the uretdione polyisocyanates A), where appropriate used together with further diisocyanates and/or polyisocyanates B), are reacted with the polyols C) and, where appropriate, further isocyanate-reactive monofunctional compounds D) in a batchwise or continuous operation, for example in special apparatus, such as intensive kneading apparatus or static mixers, in the stated equivalents ratio of isocyanate groups to isocyanate-reactive groups of from 1.8:1 to 0.6:1, preferably 1.6:1 to 0.8:1, at a reaction temperature from 40 to 200° C., more preferably from 60 to 180° C., preferably until the theoretically calculated NCO content is reached.

The reaction takes place preferably solvent-free in the melt, but can of course also be carried out in a suitable solvent which is inert towards isocyanate groups. Suitable solvents for this less preferred procedure are, for example, the conventional, customary paint solvents such as ethyl acetate, butyl acetate, ethylene glycol monomethyl or monoethyl ether acetate, 1-methoxyprop-2-yl acetate, acetone, 2-butanone, 4-methyl-2-pentanone, cyclohexanone, toluene, or mixtures thereof, but also solvents such as propylene glycol diacetate, diethylene glycol dimethyl ether, diethylene glycol ethyl and butyl ether acetate, N-methylpyrrolidone and N-methylcaprolactam, or mixtures of such solvents.

These solvents used as well where appropriate must be separated from the process product of the invention after reaction has taken place, by means of suitable methods, for example by precipitation and simple suction filtration, spray drying or melt extrusion in a devolatilizing screw.

To accelerate the urethanization reaction it is possible in the process of the invention to use the customary catalysts known from polyurethane chemistry, examples being tertiary amines such as triethylamine, pyridine, methylpyridine, benzyldimethylamine, N,N-endoethylenepiperazine, N-methylpiperidine, pentamethyldiethylenetriamine, N,N-dimethylaminocyclohexane, N,N'-dimethylpiperazine or metal salts such as iron(III) chloride, zinc chloride, zinc octoate, zinc 2-ethylcaproate, zinc acetylacetonate, tin(II) octoate, tin(II) ethylcaproate, tin(II) palmitate, dibutyltin (IV) dilaurate and molybdenum glycolate.

These catalysts are employed where appropriate in amounts of from 0.001 to 2.0% by weight, preferably 0.01 to 0.2% by weight, based on the total amount of the starting compounds used.

Irrespective of the manner of its implementation the process of the invention produces, depending on the chosen equivalents ratio of isocyanate groups to isocyanate-reactive groups, polyaddition compounds which contain uretdione groups and have a free isocyanate group content (calculated as NCO; molecular weight=42) of from 0 to 6.0% by weight, preferably from 0 to 5.0% by weight, more preferably from 0 to 4.0% by weight, a uretdione group content (calculated as $C_2N_2O_2$; molecular weight=84) of from 3 to 25% by weight, preferably from 5 to 17% by weight, more preferably from 6 to 17% by weight, and a monomeric diisocyanate content of less than 1.0% by weight, preferably less than 0.5% by weight, more preferably less than 0.3% by weight, which are solid below 40° C. and liquid above 125° C. and in particular have a melting point or melting range, determined in accordance with differential thermoanalysis (DTA), which lies within a temperature range from 40 to 110° C., more preferably within the temperature range from 50 to 100° C.

The polyaddition compounds of the invention constitute valuable starting materials for preparing polyurethane plastics by the isocyanate polyaddition process. They find use in particular as a crosslinker component in heat-curable PU powder coating materials free from blocking agents. In this utility they are notable as compared with commercially available uretdione powder coating crosslinkers of analogous construction, based on IPDI, for an increased reactivity, and produce coatings having improved chemical and mechanical resistance properties, in particular a higher elasticity.

Suitable reaction partners for the polyaddition compounds of the invention are in principle all binders known from powder coating technology which have isocyanate-reactive groups, such as hydroxyl, carboxyl, amino, thiol, urethane or urea groups, for example, which may optionally further contain unsaturated groups crosslinkable by free-radical addition polymerization. In this case the powder coating materials are crosslinked by exposure to actinic radiation in addition to the heat treatment. Polymers obtained in this way feature, for example, a greater hardness and heat distortion resistance, as a result of the higher crosslinking density. Employed with preference, however, are hydroxy-functional powder coating binders which are solid below 40° C. and liquid above 130° C. The softening temperatures of these hydroxy-functional resins as determined by differential thermoanalysis (DTA) are situated preferably within the temperature range from 30 to 120° C., more preferably within the temperature range from 35 to 110° C.

Their hydroxyl numbers are generally between 20 and 200, preferably between 30 and 130, and their number-average molecular weight (calculable from the functionality and the hydroxyl content) is generally between 400 and 10 000, preferably between 1 000 and 5 000.

Powder coating binders of this kind are, for example, hydroxyl-containing polyesters, polyacrylates or polyurethanes, as described in the abovementioned publications of the prior art, e.g. EP-A 0 45 998, or EP-A 0 254 152, but also any desired mixtures of such resins.

In order to prepare a ready-to-use powder coating material the polyaddition compounds of the invention are mixed with suitable hydroxy-functional powder coating binders, where appropriate with further auxiliaries and additives, such as catalysts, pigments, fillers or levelling agents, for example, and are unified, for example in extruders or kneaders, above the melting range of the individual components, for example 70 to 130° C., preferably 70 to 110° C., to form a homogeneous material.

In this context the polyaddition compounds of the invention and the hydroxy-functional binders may be employed in proportions such that for each hydroxyl group there are from 0.6 to 2.0, preferably from 0.6 to 1.4 and more preferably from 0.8 to 1.2 isocyanate groups, the term isocyanate groups in connection with the polyaddition compounds of the invention being understood to be the sum of free isocyanate groups and isocyanate groups present in dimeric form as uretdione groups.

The catalysts that may be used where appropriate to accelerate curing are the customary compounds known from polyurethane chemistry, as already described in connection with the process of the invention for accelerating reaction, or amidines, such as 1,5-diazabicyclo[4.3.0]non-5-ene (DBN), 1,8-diazabicyclo[5.4.0]undec-7-ene (DBU) and 1,2-dimethyltetrahydropyrimidine, for example, which have proved in accordance with the teaching of EP-A 0 803 524 to be particularly suitable catalysts for lowering the baking temperatures of uretdione powder coating crosslinkers. These catalysts can be added where appropriate in amounts from 0.01 to 5.0% by weight preferably 0.05 to 2.0% by weight, based on the total amount of organic binder, i.e. polyaddition compounds of the invention in combination with the hydroxy-functional powder coating binders, but excluding the optionally used further auxiliaries and additives.

As IR-spectroscopic investigations show, any free isocyanate groups that may be present in the polyaddition compounds of the invention undergo virtually complete reaction under the conditions of powder coating preparation. The isocyanate-group-free solid which results after the melt has cooled is subsequently ground and is freed through sieving from the grain fractions above the desired grain size, for example above 0.1 mm.

The ready-to-spray powder coating material thus prepared can be applied to the target substrates by customary powder application methods, such as electrostatic powder spraying or fluid-bed sintering, for example. In accordance with the invention it is possible to coat any desired heat-resistant substrates, such as those made of metals, wood or glass, for example.

The coatings are cured by heating at temperatures from 110 to 220° C., preferably 130 to 200° C., for example, for a period of about 10 to 30 minutes. This gives hard and elastic coatings having good solvent resistance and chemical resistance, which are distinguished by excellent levelling and very high gloss.

EXAMPLES

In the text below all percentages, with the exception of the gloss figures, are by weight. The stated uretdione group contents were determined by hot titration (30-minute boiling at reflux with excess di-n-butylamine in 1,2-dichlorobenzene followed by back-titration with hydrochloric acid).

Examples for the Preparation of the Starting Compounds A

Preparation of the Catalysts

Catalyst 1: Sodium 1,2,4-triazolate

A three-necked-flask stirring apparatus with mechanical stirrer, internal thermometer and reflux condenser was charged under dry nitrogen with 200 ml of trimethanol and 45 ml of a 30% strength methanolic solution of sodium methoxide, corresponding to 0.25 mol of sodium methoxide. 17.4 g (0.25 mol) of 1,2,4-triazole were added thereto in portions at room temperature. After the end of addition of the 1,2,4-triazole the reaction mixture was stirred at reflux temperature for 4 h. The solvent was subsequently distilled off under reduced pressure and the oily residue which remained was admixed at room temperature with 200 ml of methylene chloride. The mixture was stirred at room temperature for 15 min and the precipitated solid product was filtered off. This gave 22.5 g of sodium 1,2-4-triazolate (yield: 98% of theory) in the form of a colourless powder. The product was pure according to its $^1$H-NMR spectrum and free of the 1,2,4-triazole used Catalyst 2: Sodium 1,2,3-triazolate 17.4 g (0.25 mol) of 1,2,3-triazole were reacted with an equivalent amount of methanolic sodium methoxide solution in 200 ml of methanol by the process described for catalyst 1. The reaction mixture was worked up as described above to give 22.4 g of sodium 1,2,3-triazolate (yield: 98% of theory) in the form of a virtually colourless powder. The product was pure according to its $^1$H-NMR spectrum and free from starting material.

Catalyst 3: Sodium benzotriazolate 29.8. g (0.25 mol) of benzotriazole were reacted with an equivalent amount of methanolic sodium methoxide solution in 200 ml of methanol by the process described for catalyst 1. The reaction mixture was worked up as described above to give 34.2 g of sodium benzotriazolate (yield: 97% of theory) in the form of a virtually colourless powder. The product was pure according to its $^1$H-NMR spectrum and free from starting material.

Catalyst 4: Tetrabutylphosphonium 1,2,4-triazolate

A three-necked-flask stirring apparatus with mechanical stirrer, internal thermometer and reflux condenser was charged at room temperature under dry nitrogen with 18.0 g of a 30% strength methanolic sodium methoxide solution, corresponding to 0.1 mol of sodium methoxide. Over the course of 20 min a solution of 6.9 g (0.1 mol) of 1,2,4-triazole in 20 ml of methanol was added dropwise, after which the reaction mixture was stirred for an hour and then over the course of 20 min 41.3 g (0.1 mol) of a 71.4% strength by weight solution of tetrabutylphosphonium chloride in isopropanol (Cyphos® 443P, Cytec Industries, Neuss) were added. The commencement of addition of the phosphonium salt was followed immediately by the onset of precipitation of sodium chloride. The reaction mixture was stirred for a further hour at room temperature and filtered and finally the filtrate was concentrated to a volume of about 50 ml on a rotary evaporator at a bath temperature of 40° C. and a pressure of about 1 mbar. The residue was filtered again to give 42.5 g of a clear, almost colourless solution of tetrabutylphosphonium 1,2,4-triazolate in a methanol/isopropanol mixture. The active catalyst content according to acidimetric titration with 0.1 N HCl against phenolphthalein was 73.0% by weight; the ratio of methanol to isopropanol was determined by gas chromatography (GC) as 25.4:74.6% (area %).

Catalyst 5: Methyltrioctylammonium 1,2,4-triazolate

Using the process described for catalyst 4, 6.9 g (0.1 mol) of 1,2,4-triazole in solution in 20 g of methanol were reacted first with 18.0 g (0.1 mol) of 30% strength methanolic sodium methoxide solution and then with 80.6 g of a 50% strength solution of methyltrioctylammonium chloride (Aliquat® 336, Cognis Deutschland GmbH & Co. KG, Düsseldorf) in methanol, corresponding to 0.1 mol of methyltrioctylammonium chloride. Filtration, removal of the solvent by rotary evaporator and further filtration gave 40.3 g of methyltrioctylammonium 1,2,4-triazolate as a clear, pale yellow liquid. The active catalyst content according to acidimetric titration with 0.1 N HCl was 92.3% by weight.

Catalyst 6: Trihexyltetradecylphosphonium 1,2,4-triazolate

A three-necked-flask stirring apparatus with mechanical stirrer, internal thermometer and reflux condenser was charged at room temperature under dry nitrogen with 180.0 g of a 30% strength methanolic sodium methoxide solution, corresponding to 1.0 mol of sodium methoxide. Over the course of 45 min a solution of 69 g (1.0 mol) of 1,2,4-triazole in 200 ml of methanol was added dropwise, and the reaction mixture was subsequently stirred for 12 hours. Then over the course of one hour a solution of 518 g (1.0 mol) of trihexyltetradecylphosphonium chloride (Cyphos® 3653P, Cytec Industries, Neuss) in 60 g of methanol was added dropwise. The beginning of addition of the phosphonium salt was followed immediately by the onset of sodium chloride precipitation. The reaction mixture was stirred overnight, the precipitated sodium chloride was filtered off and the solvent was subsequently distilled off in a commercially customary thin-film evaporator at a temperature of 50° C. and a pressure of about 0.3 mbar. The residue was filtered again to give 510 g (yield: 92.6% of theory) of trihexyltetradecylphosphonium 1,2,4-triazolate as a clear, almost colourless liquid having a viscosity of 570 mPas (23° C.) and a refractive index $n_D^{20}$ of 1.4821. The residual methanol content was 0.1% by weight.

Preparation of the Uretdione polyisocyanates (Starting Materials A)

Example 1

1000 g (3.82 mol) of 4,4'-diisocyanatodicyclohexylmethane were admixed at 30° C. under dry nitrogen and with stirring with a solution of 2 g (0.022 mol) of sodium 1,2,4-triazolate (catalyst 1) in 25 ml of dimethyl sulphoxide (DMSO), whereupon the temperature of the reaction mixture rose to 39° C. owing to the heat of reaction released. After a reaction time of 60 minutes, during which the exotherm subsided again, the NCO content of the reaction mixture had dropped to 26.3% by weight, corresponding to a degree of oligomerization of 15.6%. The catalyst was then deactivated by adding 4.6 g (0.022 mol) of dibutyl phosphate. The turbidity generated in this deactivation was removed by filtration and the clear, colourless reaction mixture was freed from volatile constituents (excess diisocyanate and catalyst solvent) at a temperature of 155° C. and a pressure of 0.2 mbar. This gave a colourless uretdione polyisocyanate having a free NCO group content of 14.1% by weight, a monomeric 4,4'-diisocyanatodicyclohexylmethane content of 0.4% by weight, a viscosity (according to DIN 53 018) of more than 200,000 mPas (23° C.) and a colour number (APHA), determined on a 10% strength by weight solution in methylene chloride, of 12. The molar ratio of uretdione structures to isocyanurate structures according to $^{13}$C-NMR spectroscopy was 98.4:1.6.

Example 2

1000 g (3.82 mol) of 4,4'-diisocyanatodicyclohexylmethane were admixed at 30° C. under dry nitrogen and with stirring with a solution of 2 g (0.022 mol) of sodium 1,2,3-triazolate (catalyst 2) in 25 ml of dimethyl sulphoxide (DMSO), whereupon the temperature of the reaction mixture rose to 39° C. owing to the heat of reaction released. After a reaction time of 60 minutes, during which the exotherm subsided again, the NCO content of the reaction mixture had dropped to 26.7% by weight, corresponding to a degree of oligomerization of 14.3%. The catalyst was then deactivated by adding 4.6 g (0.022 mol) of dibutyl phosphate and the reaction mixture was worked up as described in Example 1. This gave a colourless uretdione polyisocyanate of high viscosity having a free NCO group content of 14.1% by weight, a monomeric 4,4'-diisocyanatodicyclohexylmethane content of 0.5% by weight, and a colour number (APHA), determined on a 10% strength by weight solution in methylene chloride, of 14. The molar ratio of uretdione structures to isocyanurate structures according to $^{13}$C-NMR spectroscopy was 99.1:0.9.

Example 3

1000 g (3.82 mol) of 4,4'-diisocyanatodicyclohexylmethane were admixed at 30° C. under dry nitrogen and with stirring with a solution of 3.0 g (0.021 mol) of sodium benzotriazolate (catalyst 3) in 40 ml of dimethyl sulphoxide (DMSO), whereupon the temperature of the reaction mixture rose to 37° C. owing to the heat of reaction released. After a reaction time of 60 minutes, during which the exotherm subsided again, the NCO content of the reaction mixture had dropped to 26.5% by weight, corresponding to a degree of oligomerization of 13.6%. The catalyst was then deactivated by adding 4.4 g (0.021 mol) of dibutyl phosphate and the reaction mixture was worked up as described in Example 1. This gave a colourless uretdione polyisocyanate of high viscosity having a free NCO group content of 14.0% by weight, a monomeric 4,4'-diisocyanatodicyclohexylmethane content of 0.5% by weight, and a colour number (APHA), determined on a 10% strength by weight solution in methylene chloride, of 21. The molar ratio of uretdione structures to isocyanurate structures according to $^{13}$C-NMR spectroscopy was 96.4:3.6.

Example 4

1000 g (3.82 mol) of 4,4'-diisocyanatodicyclohexylmethane were admixed at 30° C. under dry nitrogen and with stirring with a solution of 2.3 g (5.1 mmol) of catalyst 4 (tetrabutylphosphonium 1,2,4-triazolate in methanol/isopropanol), whereupon the temperature of the reaction mixture rose to 42° C. owing to the heat of reaction released. After the exotherm has subsided the batch was recatalysed after 40 minutes with a further 2.3 g (5.1 mmol) of catalyst solution. After a reaction time of 1 hour 25 minutes in total, the NCO content of the reaction mixture had dropped to 26.5% by weight, corresponding to a degree of oligomerization of 13.6%. The catalyst was then deactivated by adding 2.15 g (10.2 mmol) of dibutyl phosphate and the reaction mixture was freed from excess diisocyanate as described in Example 1 by thin-film distillation. This gave a pale yellow uretdione polyisocyanate of high viscosity having a free NCO group content of 14.2% by weight, a monomeric 4,4'-diisocyanatodicyclohexylmethane content of 0.4% by weight, and a colour number (APHA), determined on a 10% strength by weight solution in methylene chloride, of 17. The molar ratio of uretdione structures to isocyanurate structures according to $^{13}$C-NMR spectroscopy was 97.2:2.8

Example 5

1000 g (3.82 mol) of 4,4'-diisocyanatodicyclohexylmethane were degassed under reduced pressure (2 mbar) for 1 hour, then blanketed with dry nitrogen and warmed to 30° C. With stirring, 8 g (0.02 mol) of catalyst 5 (methyltrioctylammonium 1,2,4-triazolate) were added, with the reaction mixture warming to 43° C. owing to the heat or reaction liberated. After a reaction time of 70 minutes, during which the exotherm subsided again, the NCO content of the reaction mixture was 26.6% by weight, corresponding to a degree of oligomerization of 16.2%. The catalyst was then deactivated by adding 4.2 g (0.2 mol) of dibutyl phosphate and the resultant clear, colourless mixture was freed from excess diisocyanate as described in Example 1 by thin-film distillation. This gave a virtually colourless uretdione polyisocyanate of high viscosity having a free NCO group content of 14.0% by weight, a monomeric 4,4'-diisocyanatodicyclohexylmethane content of 0.3% by weight, and a colour number (APHA), determined on a 10% strength by weight solution of methylene chloride, of 10. The molar ratio of uretdione structures to isocyanurate structures according to $^{13}$C-NMR spectroscopy was 99.3:0.7.

Example 6

Uretdione polyisocyanate from 4,4'-diisocyanatodicyclohexvlmethane (A1)

1000 g (3.82 mol) of 4,4'-diisocyanatodicyclohexylmethane were degassed under reduced pressure (2 mbar) for 1 hour, then blanketed with dry nitrogen and warmed to 30° C. Subsequently, with stirring, 12 g (0.022 mol) of catalyst 6 (trihexyltetradecylphosphonium 1,2,4-triazolate) were added continuously over a reaction time of 3 hours, using a laboratory infusion pump (KDS 100, KD Scientific, Boston). After a subsequent stirring time of 30 min the NCO content of the reaction mixture was 26.2% by weight, corresponding to a degree of oligomerization of 17.1%. The catalyst was then deactivated by adding 4.6 g (0.022 mol) of dibutyl phosphate and the resultant clear, colourless mixture was freed from excess diisocyanate as described in Example 1 by thin-film distillation. This gave a virtually colourless uretdione polyisocyanate of high viscosity having a free NCO group content of 14.2% by weight, a monomeric 4,4'-diisocyanatodicyclohexylmethane content of 0.5% by weight, and a colour number (APHA), determined on a 10% strength by weight solution of methylene chloride, of 11. The product according to $^{13}$C-NMR spectroscopy contained exclusively uretdione groups. Isocyanurate structures were not detectable. The uretdione group content determined by hot titration was 17.8%.

Comparative Example 1

In Accordance with EP-A 0 317 744

1000 g (3.82 mol) of 4,4'-diisocyanatodicyclohexylmethane were admixed at room temperature under dry nitrogen and with stirring with 20 g (2% by weight) of 4-dimethylaminopyridine (DMAP) catalyst. After 5 days the virtually colourless reaction mixture had an unchanged NCO content of 31.4% by weight. In the IR spectrum as well there was no indication of uretdione groups.

Comparative Example 2

In accordance with EP-A 0 317 744

1000 g of 4,4'-diisocyanatodicyclohexylmethane were admixed as described in Comparative Example 1 with 20 g (2% by weight) of DMAP and then heated at 50° C. for 5 days. The pale yellow reaction mixture had an unchanged NCO content of 31.4% by weight. In the IR spectrum there was no indication of uretdione groups.

Comparative Example 3

In Accordance with EP-A 0 317 744

1000 g (3.82 mol) of 4,4'-diisocyanatodicyclohexylmethane were admixed at room temperature under dry nitrogen and with stirring with 100 g (10% by weight) of 4-dimethylaminopyridine (DMAP) catalyst. After 5 days the IR spectrum showed a very weakly pronounced band at 1760 cm$^{-1}$, which can be interpreted as an indication of the presence of small amounts of uretdione groups. The NCO content of the pale yellow reaction mixture had dropped from 29.0 to 28.6% by weight, corresponding to a degree of oligomerization of 1.4%.

Comparative Example 4

In Accordance with EP-A 0 45 995

1000 g (3.82 mol) of 4,4'-diisocyanatodicyclohexylmethane were admixed at room temperature under dry nitrogen and with stirring with 50 g (5% by weight) of hexamethylphosphoramide. After 5 days the virtually colourless reaction mixture had an unchanged NCO content of 31.3% by weight. In the IR spectrum there was no indication of uretdione groups.

The comparative examples show that the catalysts known from the literature for the highly selective dimerization of isocyanates, in contrast to the catalysts of the process of the invention, even in high concentrations have no activity with respect to secondary isocyanate groups or have only an extremely low activity which is completely inadequate for the industrial preparation of uretdione polyisocyanates.

Example 7

Uretdione polyisocyanate from 4,4'-diisocyanato-3,3'-dimethyldicyclohexylmethane (A2)

1 000 g (3.45 mol) of 4,4'-diisocyanato-3,3'-dimethyldicyclohexylmethane were degassed for 1 hour in vacuo (2 mbar), then blanketed with dry nitrogen and warmed to 30° C. Subsequently 10 g (0.018 mol) of the above-described trihexyltetradecylphosphonium 1,2,4-triazolate dimerization catalyst (catalyst 6) were added continuously over a reaction time of 3 hours with the aid of a laboratory infusion pump (KDS 100, KD Scientific Boston) with stirring. After a subsequent stirring period of 30 minutes the NCO content of the reaction mixture was 25.1%, corresponding to a degree of oligomerization of 13.4%. The catalyst was then deactivated by adding 4.6 g (0.022 mol) of dibutyl phosphate and the resultant clear, colourless mixture was freed from excess diisocyanate by means of a thin-film evaporator at a temperature of 155° C. and a pressure of 0.2 mbar. This gave a highly viscous virtually colourless uretdione polyisocyanate having a free NCO group content of 13.3%, a monomeric 4,4'-diisocyanato-3,3'-dimethyldicyclohexylmethane content of 0.6% and a colour number (APHA), determined on a 10% strength solution in methylene chloride, of 29. According to $^{13}$C NMR spectroscopy the product contained exclusively uretdione groups; isocyanurate structures were not detectable. The uretdione group content determined by hot titration was 15.9%.

Example 8

500 g (2.05 mol) of TMXDI were degassed for 1 hour in vacuo (2 mbar), then blanketed with dry nitrogen and warmed to 30° C. Subsequently 5 g (0.009 mol) of catalyst 6 (trihexyltetradecylphosphonium 1,2,4-triazolate) were added continuously over a reaction time of 3 hours with the aid of a laboratory infusion pump (KDS 100, KD Scientific Boston) with stirring. After a subsequent stirring period of 30 minutes the NCO content of the reaction mixture was 31.4%, corresponding to a degree of oligomerization of 7.7%. The catalyst was then deactivated by adding 1.9 g (0.009 mol) of dibutyl phosphate and the resultant clear, colourless mixture was freed from excess diisocyanate by thin-film distillation as described in Example 1. This gave a highly viscous light-coloured uretdione polyisocyanate having a free NCO group content of 15.6% by weight, a monomeric TMXDI content of 0.5% by weight and a colour number (APHA), determined on a 10% strength by weight solution in methylene chloride, of 43. According to $^{13}$C NMR spectroscopy the product contained exclusively uretdione groups; isocyanurate structures were not detectable.

The uretdione group content determined by hot titration was 18.7%.

Preparation of Starting Compounds C)

Example 9

Diol Containing Ester Groups C1)

901 g of 1,4-butanediol and 1712 g of ε-caprolactone were mixed at room temperature under dry nitrogen, 0.3 g of tin(II) octoate was added and the mixture was then heated at 160° C. for 5 hours. Cooling to room temperature gave a colourless liquid product having the following characteristics:

| | |
|---|---|
| η (23° C.): | 180 mPas |
| OH number: | 416 mg KOH/g |
| Free ε-caprolactone: | 0.1% |
| Number-average molecular weight (calc. from OH number): | 269 |

Diol Containing Ester Groups C2)

Example 10

761 g of 1,3-propanediol and 1712 g of ε-caprolactone were mixed at room temperature under dry nitrogen, 0.3 g of tin(II) octoate was added and the mixture was then heated at 160° C. for 5 hours. Cooling to room temperature gave a colourless liquid product having the following characteristics:

| | |
|---|---|
| η (23° C.): | 190 mPas |
| OH number: | 449 mg KOH/g |
| Free ε-caprolactone: | 0.3% |
| Number-average molecular weight (calc. from OH number): | 249 |

Example 11

Triol Containing Ester Groups C3)

1 341 g of 1,1,1-trimethylolpropane (TMP) and 1712 g of ε-caprolactone were mixed at room temperature under dry nitrogen, 0.3 g of tin(II) octoate was added and the mixture was then heated at 160° C. for 5 hours. Cooling to room temperature gave a colourless liquid product having the following characteristics:

| | |
|---|---|
| η (23° C.): | 2 400 mPas |
| OH number: | 546 mg KOH/g |
| Free ε-caprolactone: | 0.2% |
| Number-average molecular weight (calc. from OH number): | 308 |

Preparation of Powder Coatings and Paint Films

Example 12

Inventive 360.0 g (1.22 eq) of the uretdione polyisocyanate A1) from Example 6 were charged under dry nitrogen to a vessel, 0.26 g of dibutyltin(IV) dilaurate (DBTL) as catalyst was added and the mixture was heated to 80° C. Subsequently, over the course of 10 minutes, a mixture of 131.3 g (0.98 eq) of the diol containing ester groups C1) from Example 9, 5.5 g (0.12 eq) of 1,4-butanediol and 15.9 g (0.12 eq) of 2-ethyl-1-hexanol was added, the temperature rising to 125° C. owing to the heat of reaction liberated. After a subsequent stirring period of 5 minutes the NCO content of the reaction mixture had dropped to a figure of 0.9%. The melt was cast onto a metal sheet to cool, and a polyaddition compound of the invention containing uretdione groups was obtained in the form of a colourless solid resin. The product had the following characteristics:

| | |
|---|---|
| NCO content: | 0.9% |
| Uretdione group content (calc.): | 12.5% |
| Monomeric 4,4'-diisocyanatodicyclohexylmethane: | 0.31% |
| Melting point: | 95–100° C. |

Example 13

Inventive 360.0 g (1.22 eq) of the uretdione polyisocyanate A1) from Example 6 were charged under dry nitrogen to a vessel, 0.25 g of DBTL as catalyst was added and the mixture was heated to 80° C. Subsequently, over the course of 10 minutes, a mixture of 122.0 g (0.98 eq) of the diol containing ester groups C2) from Example 10 and 5.5 g (0.12 eq) of 1,4-butanediol was added and the reaction mixture was stirred at a maximum reaction temperature of 125° C. until after about 15 minutes its NCO content had dropped to a figure of 1.2%. The melt was cast onto a metal sheet to cool, and a polyaddition compound of the invention was obtained as a light yellow solid resin having the following characteristics:

| | |
|---|---|
| NCO content (found/calc.): | 1.2/1.0% |
| Uretdione group content (calc.): | 13.1% |
| Total NCO content (calc.): | 14.1% |
| NCO functionality: | 2.0 |
| Monomeric 4,4'-diisocyanatodicyclohexylmethane: | 0.26% |
| Melting point: | 95–110° C. |

Example 14

Inventive 350.0 g (1.11 eq) of the uretdione polyisocyanate A2) from Example 7 were charged under dry nitrogen to a vessel, 0.25 g of DBTL as catalyst was added and the mixture was heated to 80° C. Subsequently, over the course of 10 minutes, a mixture of 119.7 g (0.89 eq) of the diol containing ester groups C1) from Example 9, 3.4 g (0.11 eq) of 1,2-ethanediol and 14.3 g (0.11 eq) of 2-ethyl-1-hexanol was added, the temperature rising to 118° C. owing to the heat of reaction liberated. After a subsequent stirring period of 10 minutes the NCO content of the reaction mixture had dropped to a figure of 0.8%. The melt was cast onto a metal sheet to cool, and a polyaddition compound of the invention containing uretdione groups was obtained in the form of a colourless solid resin. The product had the following characteristics:

| | |
|---|---|
| NCO content: | 0.8% |
| Uretdione group content (calc.): | 11.4% |
| Monomeric 4,4'-diisocyanato-3,3'-dimethyldicyclohexylmethane: | 0.42% |
| Melting point: | 95–100° C. |

Example 15

Inventive 300.0 g (1.01 eq) of the polyisocyanate A1 from Example 6 containing uretdione groups were mixed at 50° C. with 50.0 g (0.60 eq) of HDI under dry nitrogen, then 0.5 g of DBTL as catalyst was added and the mixture was heated to 80° C. To this mixture, which had a uretdione group content of 15.3%, was added over the course of minutes a mixture of 64.6 g (0.48 eq) of the diol containing ester groups C1) from Example 9, 36.0 g (0.80 eq) of 1,4-butanediol and 41.6 g (0.32 eq) of 2-ethyl-1-hexanol and the reaction mixture was stirred at a maximum reaction temperature of 122° C. until after about 15 minutes its NCO content had dropped to a figure of 0.7%. The melt was poured onto a metal sheet to cool, and gave a polyaddition compound of the invention as a light yellow solid resin having the following characteristics:

| | |
|---|---|
| NCO content: | 0.7% |
| Uretdione group content (calc.): | 10.8% |
| Monomeric 4,4'-diisocyanatodicyclohexylmethane: | 0.27% |
| Monomeric HDI: | 0.0% |
| Melting range: | 93–101° C. |

Example 16

Inventive 300 g (1.01 eq) of the polyisocyanate A1 from Example 6 containing uretdione groups were mixed at 50° C. with 30 g (0.16 eq) of an HDI-based isocyanurate polyisoyanate prepared in analogy to Example 7 of EP-A 0 330 966, having a free isocyanate group content of 21.8%, a monomer HDI content of 0.1% and an average NCO functionality of 3.5 under dry nitrogen, then 0.5 g of DBTL as catalyst was added and the mixture was heated to 80° C. To this mixture, which had a uretdione group content of 16.2% and an average NCO functionality of 2.12, was added over the course of 20 minutes a mixture of 24 g (0.23 eq) of the triol containing ester groups C3) from Example 11, 47 g (0.35 eq) of the diol containing ester groups C1) from Example 9 and 16 g (0.35 eq) of 1,4-butanediol and the reaction mixture was stirred at a maximum reaction temperature of 120° C. until after about 15 minutes its NCO content had dropped to a figure of 2.8%. The melt was poured onto a metal sheet to cool, and gave a polyaddition compound of the invention as a light yellow solid resin having the following characteristics:

| | |
|---|---|
| NCO content (found/calc.): | 2.8/2.4% |
| Uretdione group content (calc.): | 12.8% |
| Total NCO content (calc.): | 15.2% |
| NCO functionality: | 5.1 |
| Monomeric 4,4'-diisocyanatodicyclohexylmethane: | 0.33% |
| Monomeric HDI: | <0.03% |
| Melting range: | 98–107° C. |

Example 17

Inventive 340.0 g (1.15 eq) of the uretdione polyisocyanate A1) from Example 6 were charged under dry nitrogen to a vessel, 0.25 g of DBTL as catalyst was added and the mixture was heated to 80° C. Then, in one portion, 185.6 g (1.38 eq) of the diol containing ester groups C1) from Example 9 was added and the reaction mixture was stirred at a maximum reaction temperature of 130° C. until after about 5 minutes all of the isocyanate groups had been reacted. The melt was poured onto a metal sheet to cool, giving a polyaddition compound of the invention as a pale yellow solid resin having the following characteristics:

| | |
|---|---|
| NCO content: | 0% |
| Uretdione group content (calc.): | 11.5% |
| Monomeric 4,4'-diisocyanatodicyclohexylmethane: | 0.23% |
| Melting point: | 103–115° C. |

Example 18

Comparative, in Analogy to EP-A 0 639 598

350.0 g (1.39 eq) of a polyisocyanate containing uretdione groups and based on 1-isocyanato-3,3,5-trimethyl-5-isocyanatomethylcyclohexane (IPDI), having a free isocyanate group content of 16.7% and a uretdione group content (determined by hot titration) of 20.9%, were admixed under dry nitrogen with 0.5 g of DBTL catalyst and heated to 80° C. Subsequently, in the course of 20 minutes, a mixture of 149.3 g (1.11 eq) of the diol containing ester groups C1) from Example 9, 6.3 g (0.14 eq) of 1,4-butanediol and 18.2 (0.14 eq) of 2-ethyl-1-hexanol was added and the reaction mixture was stirred at a reaction temperature of max. 110° C. until after about 20 minutes its NCO content had dropped to a figure of 0.7%. The melt was poured onto a metal sheet to cool, giving a polyaddition compound of the invention as a pale yellow solid resin having the following characteristics:

| | |
|---|---|
| NCO content: | 0.7% |
| Uretdione group content (calc.): | 14.0% |
| Monomeric IPDI: | 0.17% |
| Melting range: | 94–98° C. |

Example 19

Use; Inventive [a] and Comparative [b]

[a] 26.5 parts by weight of a commercial hydroxyl-containing polyester (Rucote® 182, Bayer AG) having an OH number of 30 and 24.6 parts by weight of a commercial hydroxyl-containing polyester (Rucote® 194, Bayer AG) having an OH number of 45 were mixed thoroughly with 11.4 parts by weight of the inventive polyaddition compound from Example 1, corresponding to an equivalents ratio of total NCO to OH of 1:1, 1.5 parts by weight of a commercial levelling agent (Resiflow® PV 88, Worlée-Chemie GmbH, Hamburg), 0.5 part by weight of tin(II) palmitate catalyst, 0.5 part by weight of benzoin and 35.0 parts by weight of a white pigment (Kronos 2160, Kronos Titan GmbH, Leverkusen) and the mixture was subsequently homogenized using a Buss cokneader of type PLK 46 at 100 rpm with a barrel temperature of 100 to 120° C. in the screw section. After cooling, the solidified melt was ground and sieved with the aid of a classifier mill (ACM 2, Hosokawa Milk-ropul) with a 90 μm screen.

[b] For comparison, a powder coating material was prepared analogously from 27.0 parts by weight of Rucote® 182 and 25.2 parts by weight of Rucote® 194 with 10.3 parts by weight of the polyaddition compound obtained in accordance with Comparative Example 20, 1.5 parts by weight of a commercial levelling agent (Resiflow® PV 88, Worlée Chemie GmbH, Hamburg), 0.5 part by weight of tin(II) palmitate catalyst, 0.5 part by weight of benzoin and 35.0 parts by weight of a white pigment (Kronos 2160, Kronos Titan GmbH, Leverkusen). The equivalents ratio of total NCO to OH was again 1:1.

The two powder coating materials obtained in this way were sprayed onto degreased steel panels using an ESB cup-type gun with a high voltage of 70 KV and cured in each case for 15 minutes at a temperature of 160° C., 170° C. and 180° C. to form white coatings which had levelled out smoothly. At coat thicknesses of approximately 60 μm the following coating properties were found:

Powder coating crosslinked with polyaddition compound from

|  | Example 19 (inventive [a]) | | | Example 19 (comparative [b]) | | |
| --- | --- | --- | --- | --- | --- | --- |
|  | 150° C. | 160° C. | 170° C. | 150° C. | 160° C. | 170° C. |
| EC[a] | <1 | 5.6 | 7.0 | <1 | <1 | <1 |
| Gloss[b] 20° | 82 | 83 | 81 | 80 | 82 | 82 |
| 60° | 93 | 94 | 94 | 93 | 91 | 90 |
| Ac[c] DR | 22 | 50 | 50 | 11 | 16 | 50 |
| Judgement | 3 | 1–2 | 1–2 | 3 | 3 | 2 m |

[a] EC = Erichsen cupping in accordance with DIN 53156
[b] Gloss = Garner gloss; 20° or 60° reflection angle
[c] Ac = acetone test; DR = number of double rubs with soaked cotton pad
Judgement = 0 = film intact
  1 = film surface softened
  2 = film swollen down to substrate
  3 = film dissolved
  m = matt (loss of gloss)

The comparison shows that by means of the powder coating material of the invention a fully crosslinked paint film is obtained even at a low baking temperature, the said film being distinguished by a higher elasticity than the coating produced using the known, prior art polyaddition compound.

Examples 20 to 23

Use, Inventive

In accordance with the process described in Example 18 white-pigmented powder coating materials were prepared starting from the hydroxyl-containing polyester of OH number 30 described in Example 19 (Rucote® 182, Bayer AG, Leverkusen) and the polyaddition compounds 13, 14, 15, and 16 of the invention. The ready-formulated powder coating materials were each sprayed onto degreased sheet steel using an ESB cup-type gun with a high voltage of 70 KV and cured at 170° C. for 15 minutes. The table below shows the compositions (parts by weight) of the powder coating materials and also the technical coatings data of the coatings obtained from them (coat thickness in each case approximately 60 μm).

| Example | | 20 | 21 | 22 | 23 |
| --- | --- | --- | --- | --- | --- |
| Rucote ® 182 | | 53.9 | 52.2 | 51.7 | 54.4 |
| Polyaddition compound from | Example 13 | 8.6 | — | — | — |
|  | Example 14 | — | 10.3 | — | — |
|  | Example 15 | — | — | 10.8 | — |
|  | Example 16 | — | — | — | 8.1 |
| Resiflow ® PV 88 | | 1.5 | 1.5 | 1.5 | 1.5 |
| Benzoin | | 0.5 | 0.5 | 0.5 | 0.5 |
| Tin (II) palmitate | | 0.5 | 0.5 | 0.5 | 0.5 |
| Kronos 2160 | | 35.0 | 35.0 | 35.0 | 35.0 |
| Gel time 180° C. [sec] | | 290 | 360 | 370 | 340 |
| Erichsen cupping to DIN 53156 [mm] | | 3.6 | 3.2 | 5.3 | 4.3 |
| Gloss 60°/20° (DIN 67530) | | 91/83 | 92/83 | 98/84 | 93/81 |
| Acetone test[a] | DR | 50 | 50 | 50 | 50 |
|  | Judgement | 1–2 | 1–2 | 1–2 | 1–2 |

[a] For evaluation see Example 19)

What is claimed is:

1. Polyaddition compounds containing uretdione groups obtained by reacting uretdione polyisocyanates formed from aliphatic and/or cycloaliphatic diisocyanates having exclusively secondary- and/or tertiary-attached isocyanate groups with a molar fraction of isocyanurate structures, based on the sum of uretdione groups and isocyanurate groups, of not more than 10%, with compounds reactive towards isocyanates.

2. Process for preparing polyaddition compounds according to claim 1, in which
  A) uretdione polyisocyanates formed from diisocyanates having exclusively secondary- and/or tertiary-attached isocyanate groups, with a molar fraction of isocyanurate structures, based on the sum of uretdione groups and isocyanurate groups, of not more than 10%, and optionally
  B) further diisocyanates and/or polyisocyanates in an amount of up to 70% by weight, based on the total weight of components A) and B), are reacted with
  C) polyols of the number average molecular weight range from 62 to 2 000 and optionally
  D) further isocyanate-reactive monofunctional compounds in an amount of up to 40% by weight, based on the total weight of components C) and D),
  while observing an equivalents ratio of isocyanate groups to isocyanate-reactive groups of from 1.8:1 to 0.6:1.

3. A method of preparing polyurethane plastics comprising reacting the polyaddition compounds according to claim 1 with compounds having isocyanate-reactive groups.

4. A method of preparing mouldings and shaped parts comprising reacting the polyaddition compounds according to claim 1 with compounds having isocyanate-reactive groups.

5. A method of preparing coating materials and coatings comprising mixing the polyaddition compounds according to claim 1 with compounds having isocyanate-reactive groups and one or more auxiliaries and additives selected from the group consisting of catalysts, pigments, fillers, levelling agents and combinations thereof.

6. Polyurethane plastics obtained by reacting the polyaddition compounds according to claim 1 with compounds containing isocyanate-reactive groups.

7. Powder coating formulations comprising polyaddition compounds according to claim 1.

8. Method of coating substrates, characterized in that a substrate is first coated with a powder coating formulation according to claim 7 and is then subjected to a heat treatment and/or to treatment with actinic light, in the course of which a coherent coating film forms on the substrate from the powder coating formulation.

* * * * *